United States Patent
Ali et al.

(10) Patent No.: US 11,878,043 B1
(45) Date of Patent: Jan. 23, 2024

(54) **METHOD FOR SYNTHESIZING SILVER NANOPARTICLES FROM *AMARANTHUS HYBRIDUS***

(71) Applicant: KING FAISAL UNIVERSITY, Al-Ahsa (SA)

(72) Inventors: Enas Mohamed Ali, Al-Ahsa (SA); Basem Mohamed Abdallah Abdelsalam, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/208,435

(22) Filed: Jun. 12, 2023

(51) Int. Cl.
| | |
|---|---|
| *A61K 36/21* | (2006.01) |
| *A61K 9/51* | (2006.01) |
| *A61P 31/10* | (2006.01) |
| *A61K 33/38* | (2006.01) |
| *B82Y 40/00* | (2011.01) |
| *B82Y 5/00* | (2011.01) |

(52) U.S. Cl.
CPC ............ *A61K 36/21* (2013.01); *A61K 9/5192* (2013.01); *A61K 33/38* (2013.01); *A61P 31/10* (2018.01); *B82Y 5/00* (2013.01); *B82Y 40/00* (2013.01)

(58) Field of Classification Search
CPC .................................. A61P 31/10; B82Y 5/00
See application file for complete search history.

(56) References Cited

U.S. PATENT DOCUMENTS

| 2012/0108425 A1 | 5/2012 | Gnanamangai et al. |
| 2021/0121511 A1 | 4/2021 | Lin et al. |

FOREIGN PATENT DOCUMENTS

| CN | 113996801 | * | 2/2022 |
| CN | 113996801 A | | 2/2022 |
| PL | 234470 B1 | | 2/2020 |
| WO | 2005120173 A2 | * | 12/2005 |

OTHER PUBLICATIONS

Terzieva, S., "Antimicrobial activity of *Amaranthus* spp. Extracts Against some Mycotoxigenic Fungi," Bulgarian Journal of Agricultural Science 25(3): pp. 120-123 (2019).
Rao, M. L. & Savithramma, N., "Biological Synthesis of Silver Nanoparticles using Svensonia Hyderabadensis Leaf Extract and Evaluation of their Antimicrobial Efficacy," J. Pharm. Sci. & Res. 3(3): pp. 1117-1121 (2011).

* cited by examiner

*Primary Examiner* — Carlos A Azpuru
(74) *Attorney, Agent, or Firm* — Nath, Goldberg & Meyer; Richard C. Litman

(57) ABSTRACT

*Amaranthus hybridus* silver nanoparticles can be synthesized by mixing an extract of *Amaranthus hybridus* with a silver nitrate solution to provide a mixture including *Amaranthus hybridus* silver nanoparticles. The *Amaranthus hybridus* silver nanoparticles can have an average particle size ranging from about 45 nm to about 100 nm. The AH-AgNPs can have antifungal properties and can be particularly effective agents against *Madurella mycetomatis*, for the treatment of eumycetoma.

4 Claims, 3 Drawing Sheets

METHOD FOR SYNTHESIZING SILVER NANOPARTICLES FROM *AMARANTHUS HYBRIDUS*

BACKGROUND

1. Field

The disclosure of the present patent application relates to synthesis of a silver nanoparticle composition, and particularly to synthesis of silver nanoparticles using an extract of *Amaranthus hybridus*.

2. Description Of The Related Art

Recently, nanoparticles have demonstrated important uses in a variety of fields. Nanoparticles have been used in electronics, sensing, optics, and medicine, for example.

Synthesis of nanoparticles has been achieved by a variety of methods, including physicochemical, thermal decomposition, electrochemical, microwave assisted, sonochemical, solvothermal, photosynthesis, photochemical reduction, chemical reduction and continuous-flow methods. These methods are often costly or produce by-products that pose increased risks to human health and the environment.

In particular, silver and gold nanoparticles may be used as antimicrobial agents against bacteria, viruses, and fungi, including drug-resistant strains of microorganisms. Typically, bacteria have diameters in the micron range, while viruses have diameters less than a micron in size. The fact that the silver nanoparticles are so small allows them to interact readily with such microorganisms. The antimicrobial action occurs because the silver nanoparticles interfere with the enzymatic metabolism of oxygen by the microbes, which effectively "suffocates" and kills the particular microorganism. The nanoscale size of silver nanoparticles means that the particles have a very large surface area, therefore only a small volume of silver nanoparticles is required to act as an effective antagonistic agent.

In recent years, green or environmentally friendly chemical methods have been developed to prepare nanoparticles using plant extracts. Green chemistry has the advantage of being safer, faster, environmentally friendly, and economical. However, the rise of green methods of preparing nanoparticles has also demonstrated that the activities and characteristics of the nanoparticles vary significantly, depending upon the detailed method of synthesis and specific plant extract used. Further, the therapeutic potential of plant extracts has been compromised due to the lack of controlled delivery of an effective dose to the desired target site.

Eumycetoma is a chronic subcutaneous fungal infection that spreads very slowly, starting from a primary lesion at the location of inoculation into the skin and deeper tissues, finally destroying muscles and bones. The leg and foot are the most affected organs because of inoculation through thorn pricks. The cure rates are very low, and amputation of the affected limb is generally the only solution to stop the spreading of the fungal infection.

Thus, nanoparticles synthesized using an environmentally friendly method solving the aforementioned problems are desired.

SUMMARY

The present subject matter relates to synthesis of silver nanoparticles from *Amaranthus hybridus* comprising: dissolving silver nitrate in deionized water to provide a silver solution and adding an aqueous extract of *Amaranthus hybridus* to the silver solution to provide a mixture including Amaranthus hybridus silver nanoparticles.

According to an embodiment, the present subject matter relates to a pharmaceutical composition comprising *Amaranthus hybridus* silver nanoparticles and a pharmaceutically acceptable carrier. In an embodiment, the pharmaceutical composition includes an extract of *Amaranthus hybridus*.

According to an embodiment, the present subject matter relates to a method of inhibiting fungal growth in a subject comprising administering an effective amount of the pharmaceutical composition to a subject in need thereof. In an embodiment, the fungal growth includes growth of *Madurella mycetomatis*.

According to an embodiment, the present subject matter relates to a method of treating eumycetoma in a subject comprising administering an effective amount of the pharmaceutical composition to a subject in need thereof.

These and other features of the present subject matter will become readily apparent upon further review of the following specification.

DETAILED DESCRIPTION OF THE PREFERRED EMBODIMENTS

Figure 1:
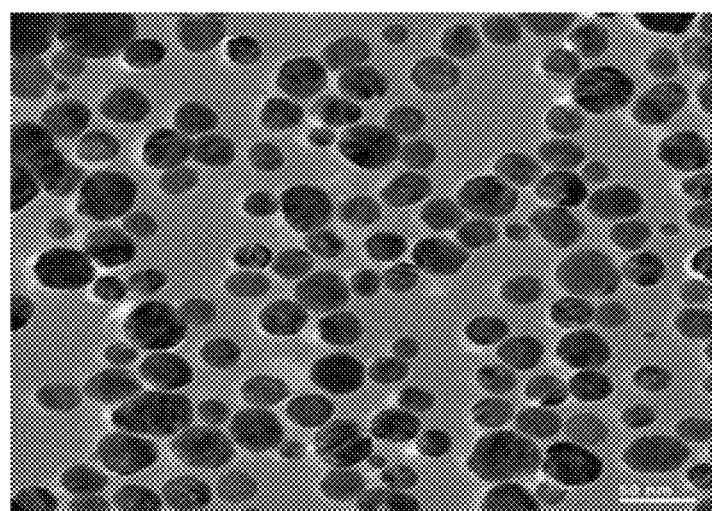
FIG. 1 is a transmission electron microscopy (TEM) image of *Amaranthus hybridus* silver nanoparticles.

The following definitions are provided for the purpose of understanding the present subject matter and for construing the appended patent claims.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to *Amaranthus hybridus* silver nanoparticles (AH-AgNPs). The *Amaranthus hybridus* silver nanoparticles may be synthesized by mixing an extract of *Amaranthus hybridus* (AH extract) with a silver nitrate solution to provide a mixture including Amaranthus hybridus silver nanoparticles AH-AgNPs or a "silver nanoparticle composition." The solution can be dried and centrifuged to isolate the silver nanoparticles. In one embodiment, the AH-AgNPs can be combined with an AH extract to provide an enhanced extract composition ("AH-AgNPs/AH").

In one embodiment, the AH extract can be a leaf extract of *Amaranthus hybridus*. In an embodiment, the AH extract can be an alcohol extract or a water extract, for example.

In an embodiment, the AH-AgNPs can have an average particle size ranging from about 45 nm to about 100 nm, or from about 46 nm to about 87 nm. In other embodiments, the AH-AgNPs can have an average particle size of about 50 nm, about 60 nm, about 70 nm, about 80 nm, or about 90 nm.

An embodiment of the present subject matter is directed to a pharmaceutical composition comprising the AH-AgNPs and a pharmaceutically acceptable carrier. In one embodiment, the pharmaceutical composition includes the AH extract, the AH-AgNps, and a pharmaceutically acceptable carrier.

An embodiment of the present subject matter is directed to a method of making a pharmaceutical composition including mixing the AH-AgNPs and optionally, the AH extract, with a pharmaceutically acceptable carrier. For example, the method of making a pharmaceutical composition can include mixing the AH-AgNPs and, optionally the AH extract, under sterile conditions with a pharmaceutically acceptable carrier with preservatives, buffers, and/or propellants to create the pharmaceutical composition.

To prepare the pharmaceutical composition, the AH-AgNPs, as the active ingredient, are intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by injection, inhalation or insufflation. The AH-AgNPs can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of the AH-AgNPs or an amount effective to treat a disease, such as a fungal infection, may be determined initially from the Examples described herein and adjusted for specific targeted diseases using routine methods.

The AH-AgNPs can have antifungal properties and can be particularly effective agents against *Madurella mycetomatis*, for the treatment of eumycetoma. The AH-AgNPs can be administered to a subject in need thereof. In an embodiment, the AH-AgNPs can be administered to a subject in need thereof to inhibit fungal growth. In an embodiment, the AH-AgNPs can be administered to a subject to inhibit the growth of *Madurella mycetomatis*.

An embodiment of the present subject matter is directed to a method of inhibiting fungal growth in a subject, comprising administering to a subject in need thereof a therapeutically effective amount of the pharmaceutical composition according to the present subject matter. In an embodiment, the fungal growth includes growth of *Madurella mycetomatis*.

An embodiment of the present subject matter is directed to a method of treating eumycetoma in a subject, comprising administering to a subject in need thereof a therapeutically effective amount of the pharmaceutical composition according to the present subject matter.

The AH-AgNPs or pharmaceutical compositions thereof can be administered to a subject by any suitable route. For example, the compositions can be administered orally (including bucally and sublingually), nasally, rectally, intracisternally, intra vaginally, intraperitoneally, topically, transdermally (as by powders, ointments, or drops), and/or parenterally. As used herein, "parenteral" administration refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation may also be contemplated, including, for example, embedding a composition of the disclosure in the body such as, for example, in a tissue, in the abdominal cavity, under the splenic capsule, brain, or in the cornea.

The present teachings are illustrated by the following examples.

EXAMPLE 1

Synthesis of Silver Nanoparticles

The silver nanoparticles were synthesized by preparing $AgNO_3$ solution in deionized water. Then, 10 mL of *Amaranthus hybridus* leaf extract was added to 90 mL of the 1 mM $AgNO_3$ solution and kept in a water bath at 90° C. for 60 minutes for reduction of silver ions. The color changed from colorless to dark brown, designating the biosynthesis of silver nanoparticles.

EXAMPLE 2

Size and Morphology of AH-Ag NPs

The size and morphology of *Amaranthus hybridus* silver nanoparticles (AH-AgNPs) were studied by transmission electron microscopy (TEM) images. The average size of the AH-AgNPs was about 46 nm, although some particles were about 100 nm (FIG. 1).

Figure 2:
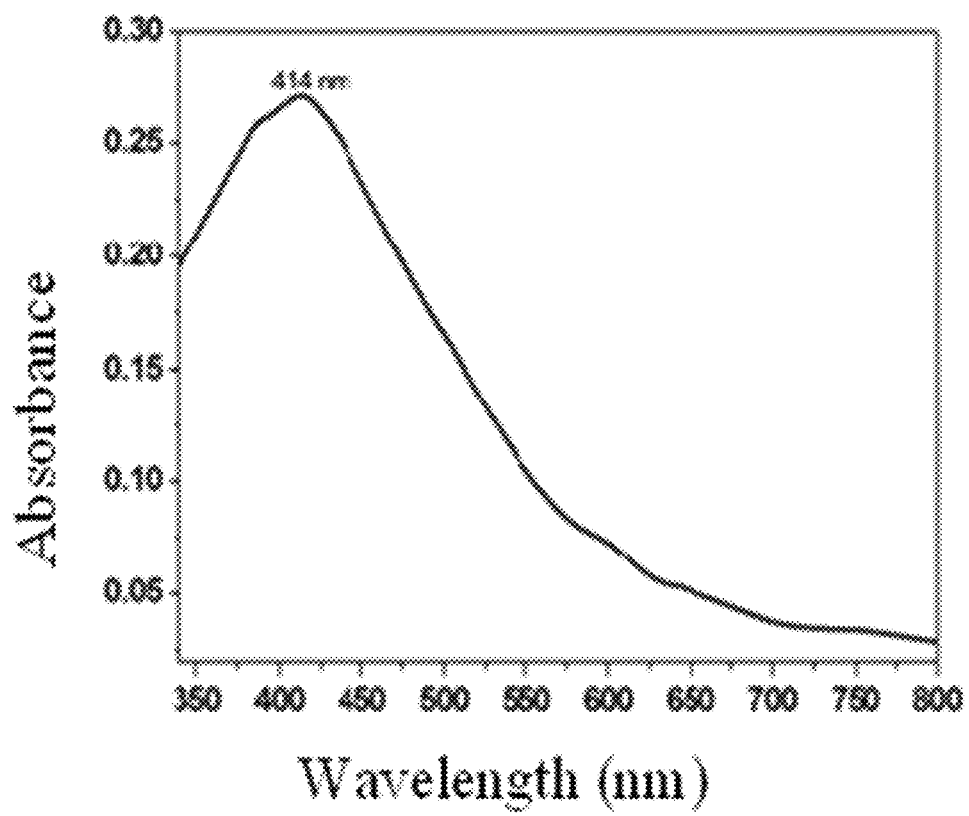
FIG. 2 shows absorption spectra of *Amaranthus hybridus* silver nanoparticles.
Figure 3:
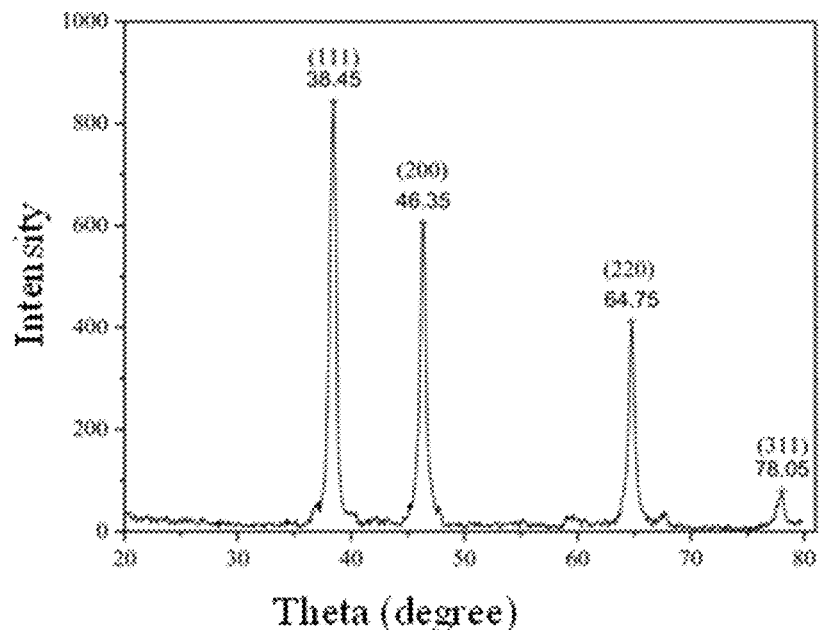
FIG. 3 shows X-ray crystallography results of *Amaranthus hybridus* silver nanoparticles.

The reduced silver was subjected to analysis by the UV-Vis spectrophotometer. Absorption spectra of AH-Ag-NPs formed in the reaction media had an absorbance peak at 414 nm (FIG. 2). The crystalline nature of nanoparticles was confirmed by X-ray crystallography (FIG. 3).

Figure 4:
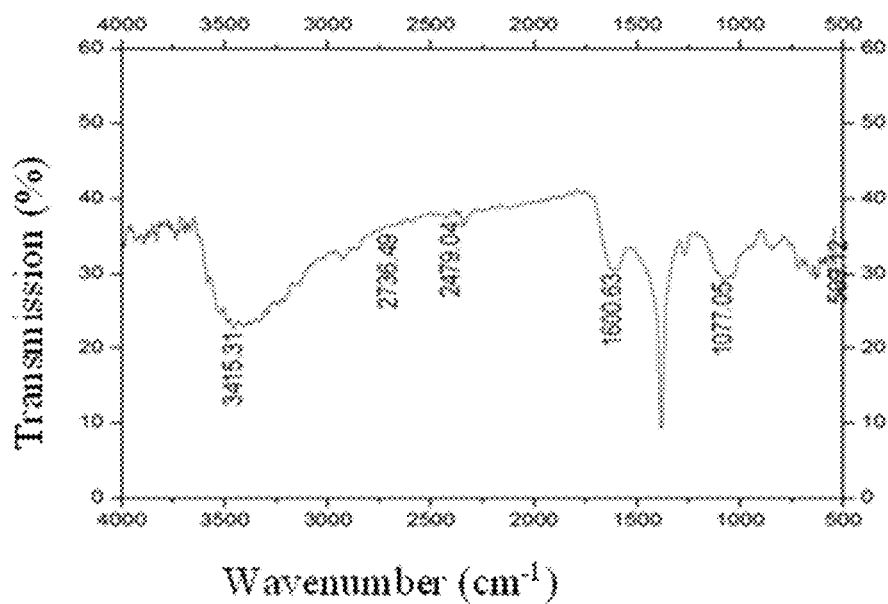
FIG. 4 shows Fourier transform infrared (FTIR) spectra of *Amaranthus hybridus* silver nanoparticles.
Figure 5:
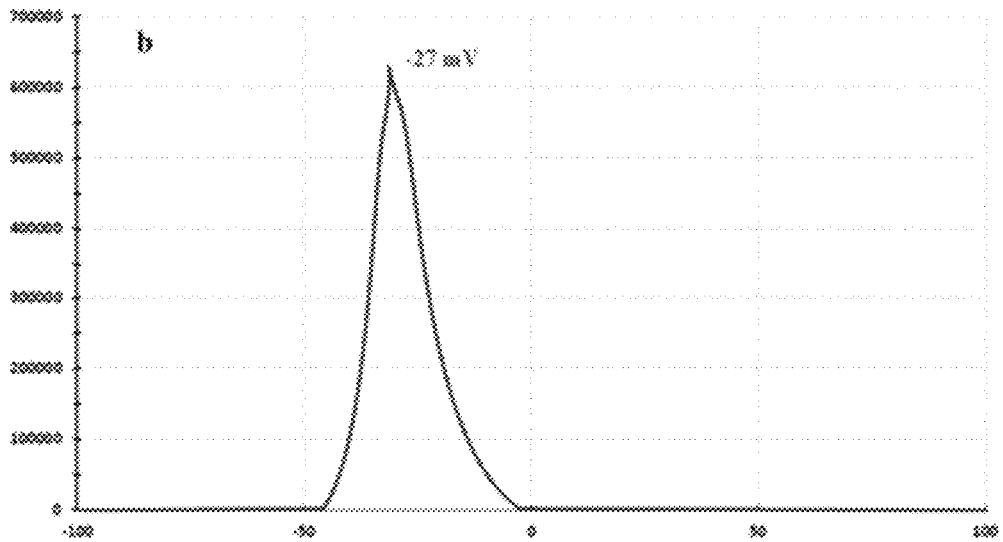
FIG. 5 is a graph showing zeta potential of the *Amaranthus hybridus* silver nanoparticles.

FIG. 4 shows the Fourier transform infrared (FTIR) spectra of the AH-AgNPs. revealed transmittance peaks at 509.12 $cm^{-1}$, 1,077.05 $cm^{-1}$ (C—O stretch alcohols), 1,600.63 $cm^{-1}$ (N—H bend amines), 2,736.49 and 2,479.04 $cm^{-1}$ (O—H stretch of carboxylic acids), and 3,415.31 $cm^{-1}$ (N—H stretching due to amines group). The peaks at 1,620-1,636 $cm^{-1}$ indicate carbonyl groups from polyphenols. The peak at 1,381 $cm^{-1}$ represents the C—N stretching of the aromatic amine group (FIG. 4). AH-AgNPs were found to carry negative zeta potential of −27 mV, which designates the repulsion between AgNPs and increases the stability of the preparation (FIG. 5).

EXAMPLE 3

Anti-fungal Activity of AH-Ag-Nps and Amaranthus hybridus extract (AH)

Figure 6:
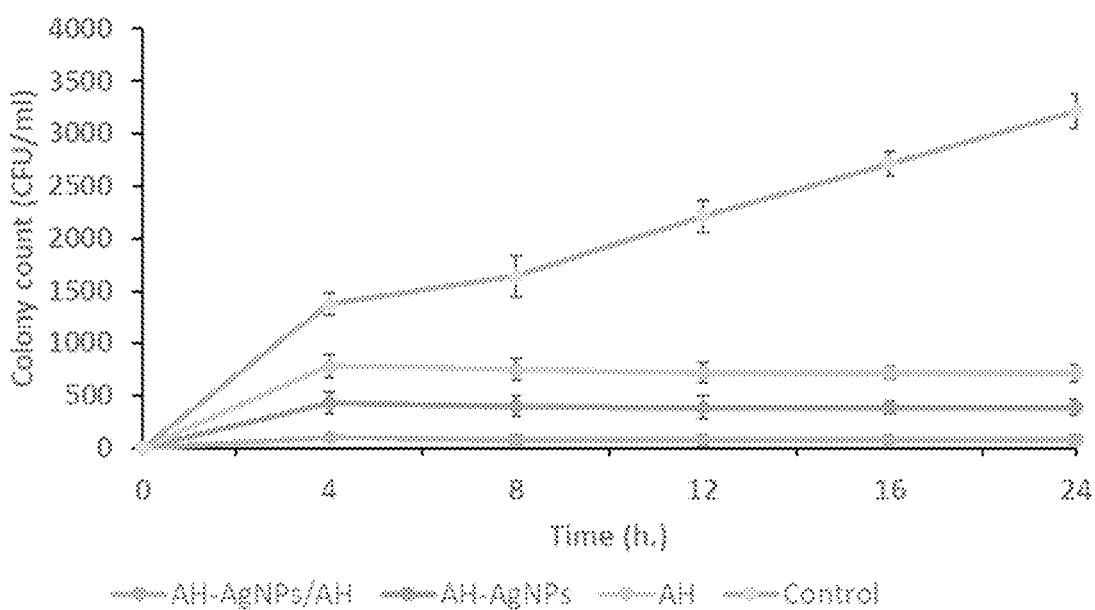
FIG. 6 is a graph showing results of a time-kill assay of the effect of the plant extract "AH" (100 µg/mL), AH-AgNPs (50 µg/mL), and AH-AgNPs/AH (50/100 µg/mL) on *Madurella mycetomatis* cells (*Madurella mycetomatis* cells treated with DMSO were used as a control).

The effectiveness of the nanoparticle composition to control growth of *Madurella mycetomatis* for treatment of eumycetoma was tested. The antifungal potential of the *Amaranthus hybridus* (AH) extract, the combination of the *Amaranthus hybridus* extract (AH) with the AH-AgNPs (AH-AgNPs/AH), and the AH-AgNPs was tested by measuring radial growth inhibition. The AH-AgNPs displayed a higher antifungal action where the MIC of AH-AgNPs and plant extract were 50 and 100 μg/mL, respectively. Interestingly, AH- AgNPs/AH displayed synergistic antifungal potential against *Madurella mycetomatis*. Furthermore, the time-kill curves showed the fungistatic action of both AH-AgNPs and plant extract at 50 and 100 m/mL, respectively, on the growth of *Madurella mycetomatis* cells (FIG. 6). After 8 h of incubation, the AH-AgNPs/AH completely repressed the growth of *Madurella mycetomatis*. Thus, AH-AgNPs/AH exhibited a greater antifungal action than the AH-AgNPs or the plant extract.

It is to be understood that the nanoparticles described herein are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of synthesizing *Amaranthus hybridus* silver nanoparticles, comprising: mixing an extract of *Amaranthus hybridus* with a silver nitrate solution to provide *Amaranthus hybridus* silver nanoparticles, the silver nanoparticles have an average particle size ranging from about 45 nm to about 100 nm.

2. *Amaranthus hybridus* silver nanoparticles prepared according to the method of claim 1.

3. A pharmaceutical composition, comprising the *Amaranthus hybridus* silver nanoparticles of claim 2 and a pharmaceutically acceptable carrier.

4. The pharmaceutical composition of claim 3, further comprising an additional amount of an extract of *Amaranthus hybridus*.

\* \* \* \* \*